US008338786B2

(12) United States Patent
Albrecht

(10) Patent No.: US 8,338,786 B2
(45) Date of Patent: Dec. 25, 2012

(54) TOMOGRAPHY ARRANGEMENT AND METHOD FOR MONITORING PERSONS

(75) Inventor: Herbert Albrecht, Baunach (DE)

(73) Assignee: Siemens Aktiengesellschaft, München (DE)

( * ) Notice: Subject to any disclaimer, the term of this patent is extended or adjusted under 35 U.S.C. 154(b) by 531 days.

(21) Appl. No.: 12/545,118

(22) Filed: Aug. 21, 2009

(65) Prior Publication Data
US 2010/0059679 A1 Mar. 11, 2010

(30) Foreign Application Priority Data

Sep. 5, 2008 (DE) .................. 10 2008 046 023

(51) Int. Cl.
*G01J 5/02* (2006.01)
*A61B 1/06* (2006.01)
(52) U.S. Cl. .................. 250/339.06; 348/61; 348/77
(58) Field of Classification Search ............ 250/339.01, 250/339.05, 361 R–370.15; 348/61, 77
See application file for complete search history.

(56) References Cited

U.S. PATENT DOCUMENTS

| 5,877,732 A * | 3/1999 | Ziarati ............... 345/8 |
| 6,175,610 B1 * | 1/2001 | Peter ............... 378/8 |
| 6,246,321 B1 * | 6/2001 | Rechsteiner et al. ......... 340/522 |
| 6,774,929 B1 * | 8/2004 | Kopp ............... 348/61 |
| 7,433,503 B2 * | 10/2008 | Cherek et al. ............. 382/128 |
| 2002/0118280 A1 * | 8/2002 | Medlar et al. .............. 348/77 |
| 2002/0188194 A1 * | 12/2002 | Cosman ............... 600/426 |

FOREIGN PATENT DOCUMENTS

| DE | 10210050 A1 | 12/2003 |
| DE | 102004033907 A1 | 2/2006 |

OTHER PUBLICATIONS

Communication From Chinese Patent Office (pp. 1-6) with English Translation (pp. 1-6), Apr. 26, 2012.

* cited by examiner

*Primary Examiner* — Kiho Kim
*Assistant Examiner* — Casey Bryant

(57) ABSTRACT

The invention relates to a tomography arrangement with a tubular measuring chamber and a monitoring facility. This monitoring facility includes at least one first video camera focusing on the measuring chamber and at least partially optically recording the same, said first video camera operating in the non-visible light wave range, in order to record moving images and an image output unit for outputting the moving images as well as a first illumination facility focusing on the measuring chamber, which, during operation, illuminates the measuring chamber in the same light wave region, in which light wave range the first video camera operates. The invention also relates to a method for monitoring persons.

16 Claims, 6 Drawing Sheets

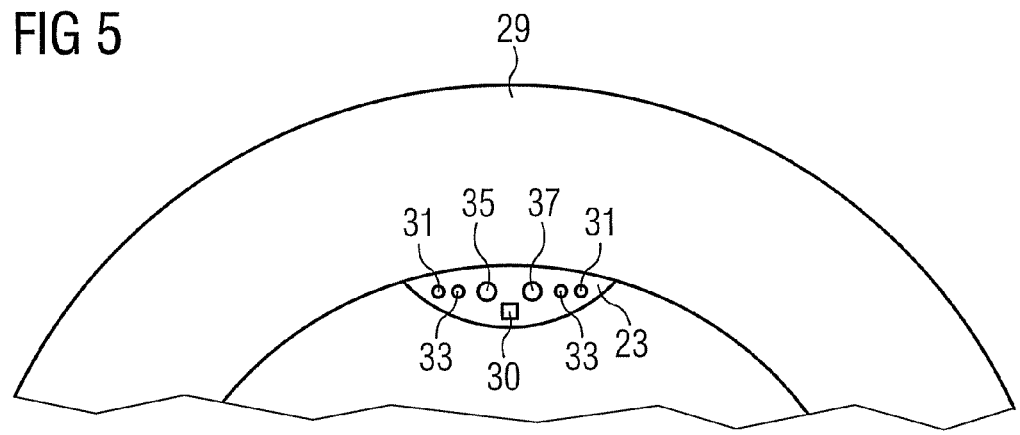
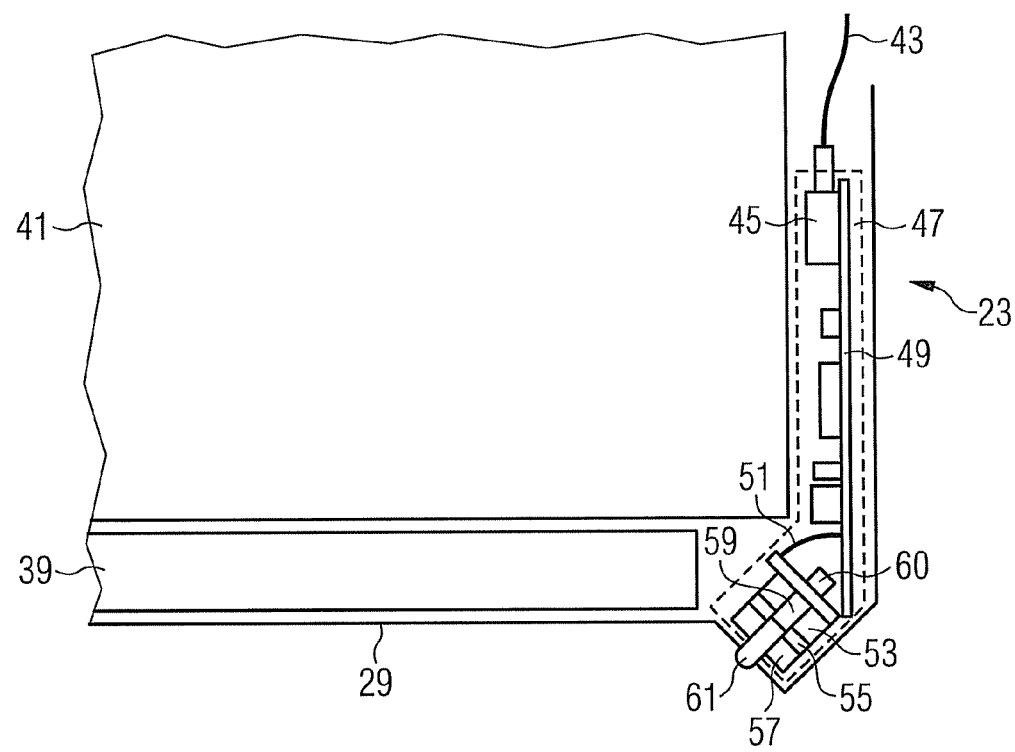

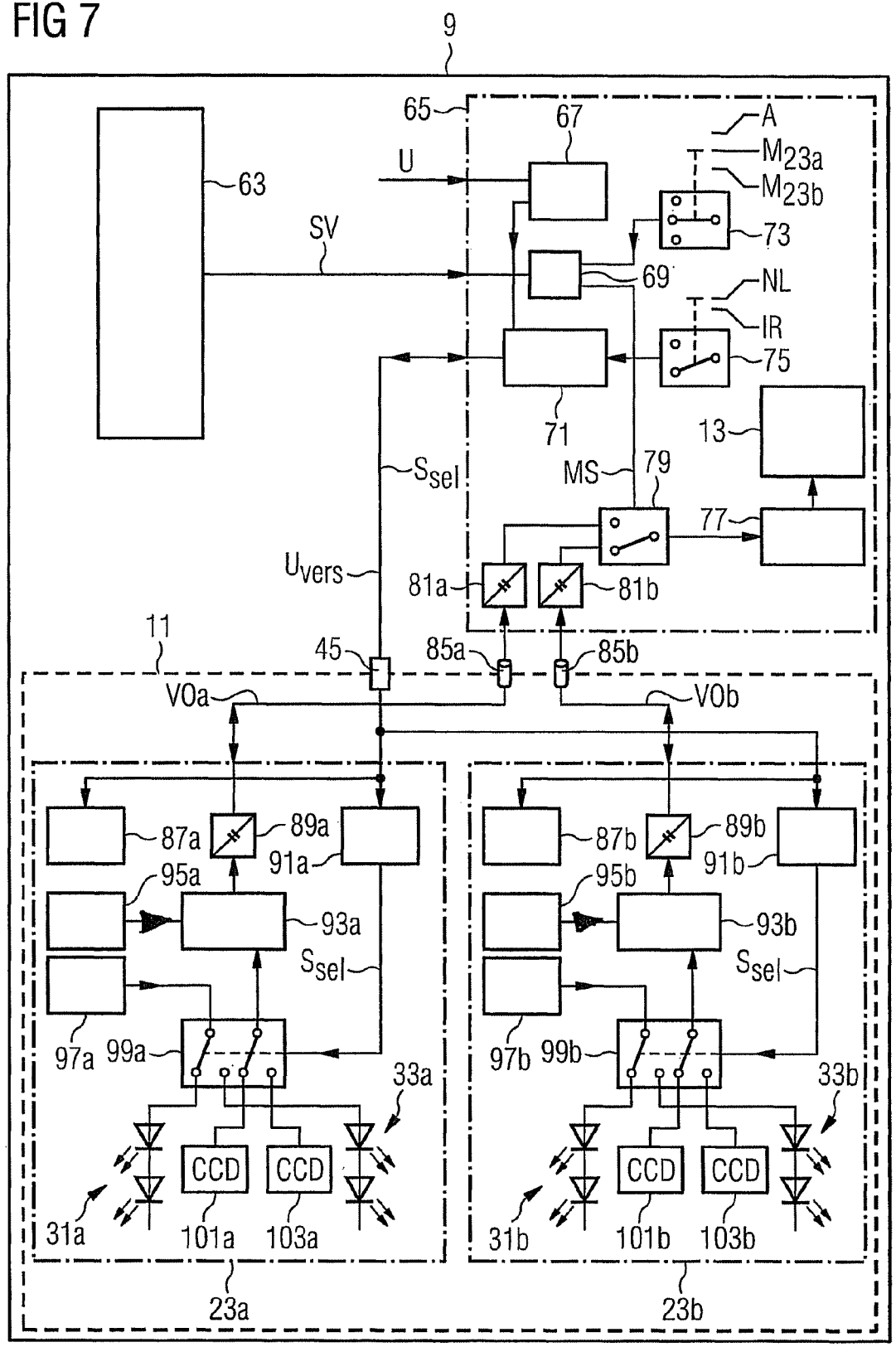

TOMOGRAPHY ARRANGEMENT AND METHOD FOR MONITORING PERSONS

CROSS REFERENCE TO RELATED APPLICATIONS

This application claims priority of German application No. 10 2008 046 023.0 filed Sep. 5, 2008, which is incorporated by reference herein in its entirety.

FIELD OF THE INVENTION

The present invention relates to a tomography arrangement with a tubular measuring chamber, into which persons can be introduced for an examination, and a monitoring facility focusing on the measuring chamber and at least partially optically recording the same in order to record moving images. The monitoring facility is used both to record the current well-being of the patient as well as to detect possible movements of the patient during the imaging. It also relates to a method for monitoring persons in a tubular measuring chamber of a tomography system.

BACKGROUND OF THE INVENTION

Within the framework of imaging methods such as magnetic resonance tomography (MR), computed tomography (CT), positron-emission tomography (PET) or single-proton-emission computed tomography (SPECT), persons are usually introduced into a tubular measuring chamber. Understood here are such measuring chambers which do not take the form of closed tubes, but instead encompass a C-shaped measuring chamber, i.e. tubes which are open on one side of a patient.

Special patients, like for instance unconscious, seriously injured or sedated patients, small children or patients with phobias must be accompanied during an imaging scan in a particularly vigilant fashion by the operating personnel. It may therefore be necessary to permanently visually monitor the location and/or the physical health of the patient in order for instance to identify a deterioration in the health as well as the appearance of problems such as disorientation and anxiety and to promptly counteract these.

If such visual monitoring is not possible directly from the site of the system controller of the imaging system, for instance if an operator of the imaging system has no direct visual contact, for instance through a window, with the patient, a video monitoring system may be helpful. Such video monitoring may then also be necessary if the movements of a patient are to be monitored automatically, so that it is not imperative that an operator permanently intensively supervises the patient during the imaging procedure, but instead is able to concentrate more on the parameter settings of the respective device for instance.

Video monitoring systems for imaging systems are currently already known. They are usually realized with the aid of a video camera, which has been retrospectively and/or additionally fastened to a wall of the chamber, in which the tomography device is positioned, during the system installation of the tomography arrangement. Alternatively, a video camera can also be attached to a casing, for instance the magnet casing of a magnetic resonance tomograph.

DE 102 10 050 A1 discloses a camera system as the basis for a relative positioning of a patient. An image matching with previous image recordings from the same perspective can take place by image recording with two independent recording axes from at least video cameras. This image matching is used as a basis for an accurate repeated positioning of a patient on one and the same site in a tomography arrangement. The video cameras can operate here in the visible and/or infrared light wave range. Patient monitoring is not provided here.

DE 101 09 219 A1 discloses a further camera-based system with a similar design with the same purpose in terms of accurate positioning.

A few disadvantages result with the known video camera systems however. For instance, the camera viewing range cannot be adapted as a function of the patient positioning. This is the case for instance when introducing the patient head first into an examination room. The facial region here is only poorly visible and/or in the case of particularly large patients the middle body region covers other body regions of the patient. The field of view of the patient can also not be monitored if in the case of MR examinations closed head coils cover the head and/or the face of the patient in the viewing direction of the camera. Different customer wishes in respect of the display of the patient's field of view and/or a certain patient region in the measuring centre in the case of any patient position could thus previously not be completely covered in such camera solutions. One further problem consists in the additional assembly effort of the camera onto the wall. Furthermore, when assembling the camera onto the magnet casing, the region in front of the measuring chamber is itself restricted by the camera and is thus only accessible for an operator with limitations if a patient is also to be treated during the imaging procedure at the same time.

A monitoring in the case of examinations with lower levels of ambient brightness was however previously impossible. To this end, particular note should be taken of the surrounding patient illumination being intentionally switched off during the examination of sedated patients for instance, in order to aid the calming of the patient by means of a darker environment. This precautionary measure nevertheless conflicts with the particularly high safety requirements in the case of sedated patients, which have to be observed as accurately as possible in order to be able to respond promptly in the event of dangerous situations.

SUMMARY OF THE INVENTION

The object of the present invention is thus to realize an improved, in particular more effective video camera system within a tomography arrangement, which is tailored in particular to special requirements in the case of monitoring sedated patients.

This object is achieved in accordance with the invention by a tomography arrangement and a method for monitoring persons as claimed in the claims.

Accordingly, an inventive tomography arrangement has a tubular measuring chamber and a monitoring facility, with the monitoring facility having at least one first video camera focusing on the measuring chamber and at least partially optically recording the same, said video camera operating in the non-visible light wave range, in order to record moving images and an image output unit for outputting moving images, as well as a first illumination facility focusing on the measuring chamber, which, during operation, illuminates the measuring chamber in the same light wave range in which the first video camera operates.

With the aid of a first video camera, which operates in the non-visible light wave range, a user is independent of the illumination situation by means of daylight and/or artificial light in the light wave range. By way of example, this means on the one hand that sedated patients are not disturbed by visible light and on the other hand that the conventional formation of shadows, which are caused by body parts of the patient, is less interfering.

It is assumed within the scope of the invention that a first video camera then operates in the non-visible light wave range, if its recording spectrum includes at least the non-visible light wave range, preferably however if the first video camera is set up accordingly with optical filter apparatuses or by adjusting its recording sensitivity exclusively to this light wave range, at least temporarily, preferably however continuously.

According to the invention, the tomography arrangement also comprises a first illumination facility focusing on the measuring chamber, said illumination facility, during operation, illuminating the measuring chamber in the same light wave range in which the first video camera operates. The first illumination facility and the first video camera therefore correspond in the light wave range; LEDs are preferably used here for the illumination facility. Such an illumination facility is used to illuminate the measuring chamber, for instance using infrared radiation. In fact an infrared video camera can also generate moving images without illumination on the basis of the thermal radiation of the patient. The image quality is however significantly improved by additionally irradiating the patient with IR light. This promptly identifies if a patient is moving. Since the light radiation is in the non-visible range, it is not disturbing for the patient.

The said object is also achieved by a method for monitoring persons in a tubular measuring chamber of a tomography arrangement, by generating image recordings in the non-visible light wave range by means of a first video camera operating in the non-visible light wave range, said video camera focusing on the measuring chamber and a display of the image recordings with the aid of an image output unit, with the measuring chamber being illuminated as a function of the light wave range, in which the first video camera is operated. Similarly to the inventive tomography arrangement, the method for monitoring persons is also based on the acquisition of moving images based on non-visible light waves while simultaneously illuminating the measuring chamber as a function of the light wave range of the first video camera, with the afore-cited advantages resulting.

Further particularly advantageous embodiments and developments of the invention also result from the dependent claims as well as the subsequent description. The method for monitoring persons can also be developed here according to the dependent claims for the tomography arrangement.

The non-visible light wave range particularly preferably includes the infrared range. Proven camera and image processing technologies already exist for infrared recordings so that a correspondingly configured monitoring facility of a tomography arrangement can be easily provided. So-called thermal images can also be generated by means of infrared recordings, i.e. recordings which are based on the radiation of patient body heat in the measuring chamber. If the patient moves, this can be identified with the aid of such infrared thermal images.

It is essentially possible within the scope of the invention for the monitoring facility to exclusively have a first video camera, which operates in the non-visible light wave range. According to an advantageous development, the monitoring facility includes a second video camera, which operates in the visible light wave range. The first video camera, which operates in the non-visible light wave range, is supplemented by the second video camera, they are complementary in respect of one another. There is thus an option to choose which camera system is preferred in the respective application for instance, because better recording images can be generated as a result thereof or because an optimal illumination situation can be produced on the basis of certain light wave ranges.

Within the scope of one embodiment with a video camera, which operates in the visible light wave range, an advantageous development consists in the tomography arrangement including a second illumination facility focusing on the measuring chamber, said illumination facility, during operation, illuminating the measuring chamber in the same light wave range in which the second video camera operates.

The advantages of this development result in a similar manner to the previously mentioned example of an illumination and a first video camera in the non-visible light wave range.

The monitoring facility particularly preferably includes a camera unit with at least two of the following components in a common housing:
the first video camera,
the first illumination facility,
the second video camera,
the second illumination facility.

All cited components are particularly preferably integrated in a double camera unit. It is however already advantageous for at least the cameras attuned to one another in the respective light wave range and illumination facilities to be part of a camera unit, because no shadows are produced as a result in the viewing range of the respective camera: the viewing direction of the camera and the illumination direction of the illumination facility are essentially the same.

Furthermore, the inventive tomography arrangement can preferably include a switchover facility between an operation of the first video camera and an operation of the second video camera. Through this an operator can automatically determine the method mode with which he wishes to monitor the respective tomography scan, taking the respective patient into consideration.

If the measuring chamber is illuminated as a function of the respective light wave range in which a video camera is operated, corresponding advantages also result similarly to switching over between the video cameras of different types.

The tomography arrangement particularly preferably has a sensor facility, which during operation determines the available brightness in the visible and/or non-visible range in the measuring chamber. The sensor facility is preferably coupled to the switchover facility for automatically switching between operation of the first video camera and operation of the second video camera as a function of the determined brightness.

A corresponding sensor facility can advantageously also be coupled to an activation and/or deactivation circuit for activating and/or deactivating illumination facilities.

The first video camera and/or the second video camera are particularly preferably directly attached in a housing of the tomography arrangement to an input region and/or output region of the measuring chamber, in a particularly advantageous fashion to the upper region of the measuring chamber. This produces the best recording angle and/or the widest and deepest coverage of the video recording. It is also advantageous that no additional attachment apparatus is needed for the respective camera, but instead that this is directly positioned where a patient can best be monitored.

An advantageous development of this embodiment provides for a first and/or a second video camera to be attached at least to two ends of the measuring chamber. A first and a second video camera are particularly preferably attached to both ends of the measuring chamber. A first and a second video camera may however also be attached to only one end of the measuring chamber and only one of the two video cameras may be attached to the other end. A "minimal version" of the development provides for only one video camera to be provided on one end of the measuring chamber in each instance, in other words either a first video camera on one end or a second video camera on the other end or two first video cameras or two second video cameras on both ends. By attaching video cameras to both ends, preferably to the entrance of the measuring chamber tubes and to its exit, a patient can be simultaneously recorded from the front and the back of the measuring chamber in the insertion direction and no significant formation of shadows, which would prevent a complete overview across the patient, are to be feared. It is possible to ensure in particular that the face of the patient can be recorded, which in most instances firstly enables an interpretation in respect of locating the patient. The development experiences an additional effect as a result of a switchover facility, which toggles between a display of image recordings and/or an operation of the video camera at one end and the other end of the measuring chamber. It is also particularly preferred for the tomography arrangement to comprise at least two camera units on both ends of the measuring chamber.

It has proven particularly advantageous for the first video camera to be coupled to the first illumination facility and/or the second video camera to be coupled to the second illumination facility such that the respective video camera and the respective illumination facility are automatically operated together. This ensures that an assignment error, for instance on the part of an operator, is impossible.

One particularly advantageous development of the invention consists in an automatic movement recognition facility based on image data recorded by the first video camera and/or the second video camera. With its help, it is possible to ensure that movements of patients within the measuring chamber are automatically detected and a warning signal can be emitted for instance, which is directed to the operator of the tomography arrangement. This ensures that potential problems within the measuring chamber can be promptly identified without an operator having to pay full attention thereto all the time. The operator may instead attend more to the parameter setting (optimal sequence parameter, optimization of the examination region on the basis of the diagnosis of already obtained recording data etc.) of the tomography device for instance.

According to a further advantageous embodiment of the invention, at least one first video camera and/or second video camera is equipped with a wide angle lens to better record the measuring chamber. This allows the measuring chamber to be monitored with improved coverage.

Furthermore, at least one first video camera and/or second video camera can be equipped with a multispectral camera and with a light wave filter. In this case, the first video camera and the second video camera can take the form of an integrative camera, in which a switchover between two different light wave filters is made. For instance, the selection of the illumination facilities can then be coupled with the respective functional mode and/or the selected wave length range, depending on whether the camera functions as the first video camera operating in the non-visible light wave range or as the second video camera functioning in the visible light wave range.

BRIEF DESCRIPTION OF THE DRAWINGS

The invention is described again in more detail below with reference to the appended figures on the basis of exemplary embodiments. Here, the same components are provided with identical reference characters in the different figures, in which;

FIG. 5 shows a top view onto a double camera unit integrated into the housing of the tomography arrangement viewed from the measuring chamber inside the tomography arrangement, FIG. 6 shows a schematic longitudinal section through the double camera unit according to FIG. 5, FIG. 7 shows a schematic circuit diagram of a monitoring facility for an inventive tomography arrangement.

DETAILED DESCRIPTION OF THE INVENTION

Figure 1:
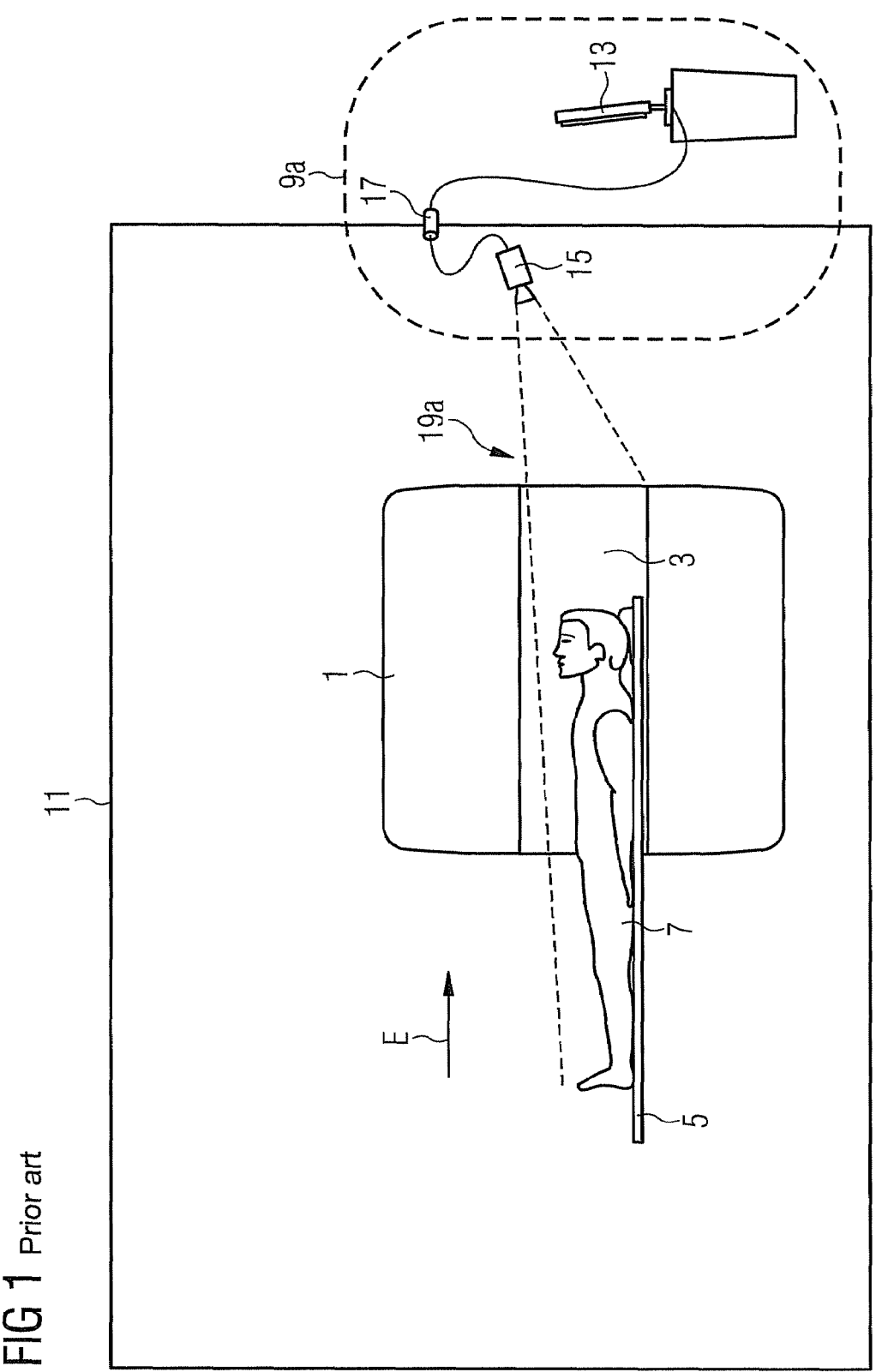
FIG. 1 shows a schematic display of a tomography arrangement according to the prior art.

FIG. 1 shows a tomography arrangement 1, here a magnetic resonance tomograph, according to the prior art. It is in an examination room 11 and essentially consists of a tube, which forms a measuring chamber 3, in which a patient couch 5 is arranged, upon which a patient 7 can be introduced into the measuring chamber 3 in the insertion direction E. It also has a monitoring facility 9a. This consists of an image output unit 13 outside the examination room 11, here a computer terminal, and a video camera 15 assembled on a wall of the examination room 11, said video camera being connected to the image output unit 13 by way of optical cables and a feedthrough waveguide 17. The video camera 15 is focused on the measuring chamber 3 and operates in the visible light wave range. With an optimal alignment of the video camera 15, a patient 7 can be recorded in a recording angle range 19a and his/her movements can be identified on the image output unit 13. The further the video camera 15 is from the housing of the tomography arrangement 1, the greater also its recording range within the measuring chamber 3, and the harder however it is to identify movements and the more shadows can therefore be cast by individual body parts of the patient 7, for instance caused by the head, so that subareas arranged in the shadow can only be identified with difficulty or not at all.

Figure 2:
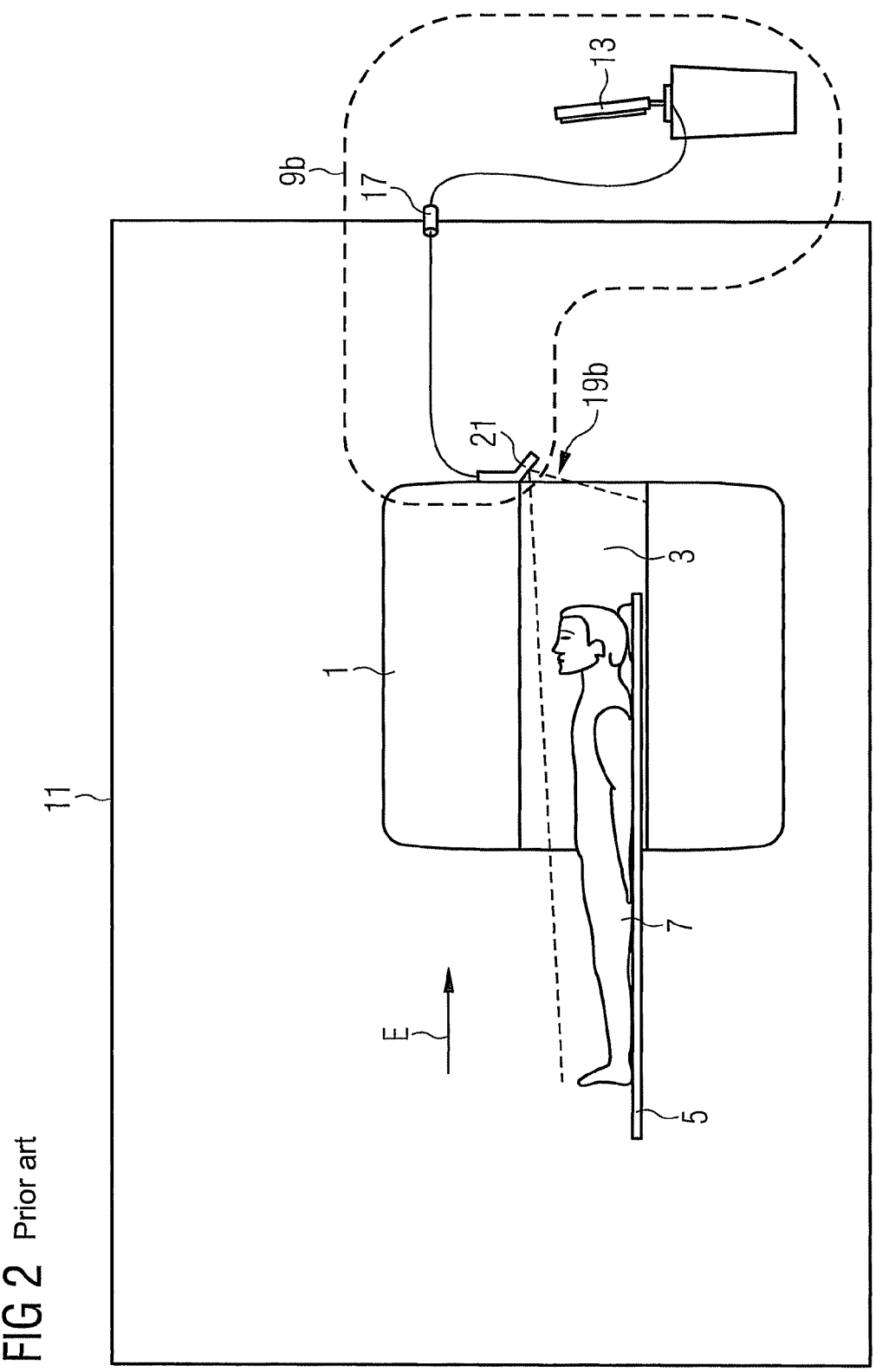
FIG. 2 shows a schematic display of an alternative embodiment of a tomography arrangement according to the prior art.

FIG. 2 shows a similar display of a prior art with a video camera 21 directly attached to the exterior of the tomography arrangement 1, said video camera having a different recording angle range 19b as a result of its close proximity to the measuring chamber 3. It also operates in the visible light wave range. It forms part of a monitoring facility 9b which is embodied in a similar fashion to FIG. 1, said monitoring facility 9b only differing from the embodiment in FIG. 1 in terms of type and attachment of the video camera 21.

Figure 3:
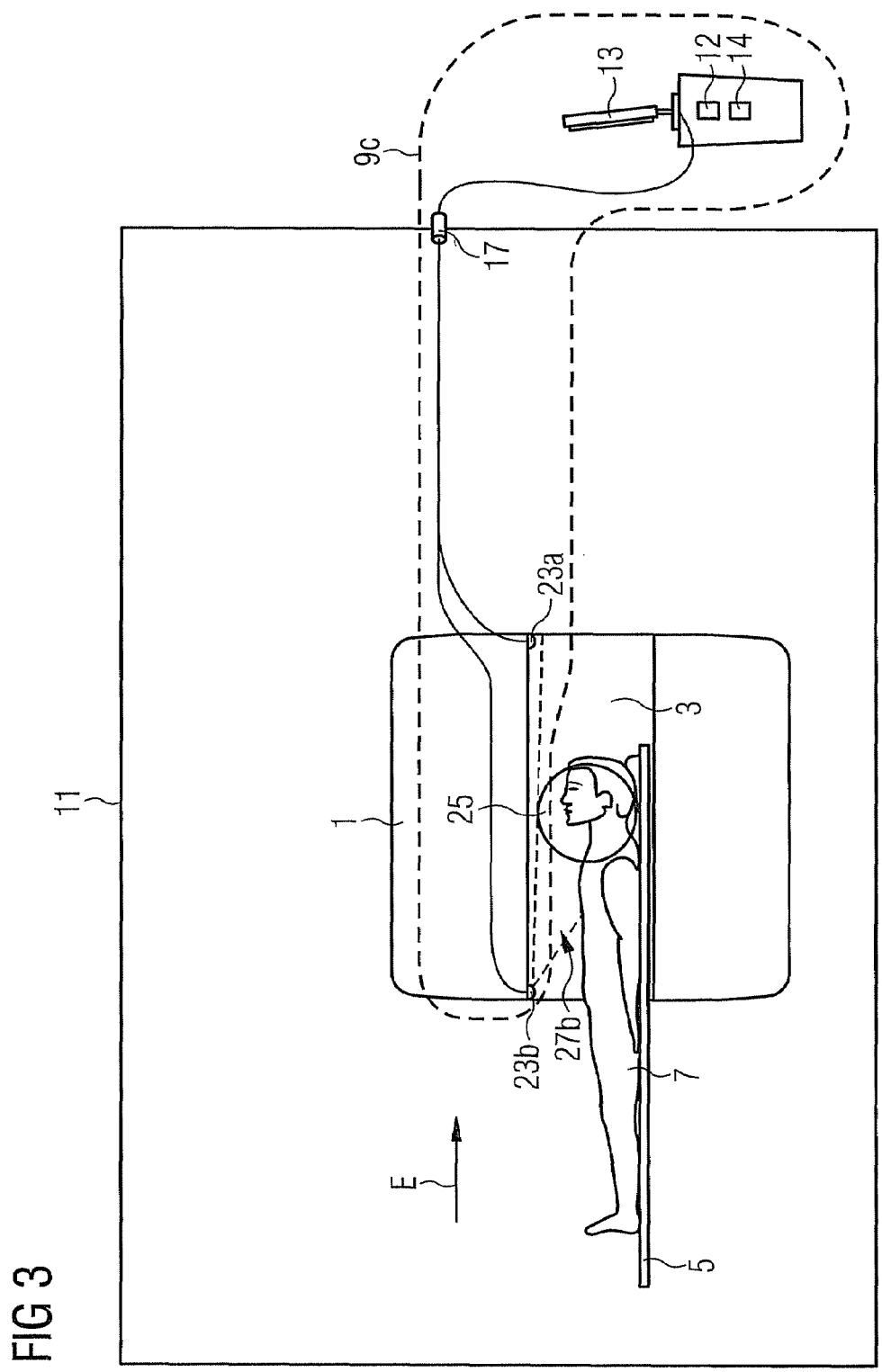
FIG. 3 shows a schematic display of an embodiment of an inventive tomography arrangement.

In contrast, FIG. 3 shows an exemplary embodiment of an inventive tomography arrangement 1 comprising a monitoring facility 9c. The monitoring facility 9c includes two double camera units 23a, 23b. At least one first video camera is contained therein (not shown—cf. FIG. 5), and operates in the non-visible light wave range. The double camera units 23a, 23b are attached within the measuring chamber 3 to its start and to its end. This produces a particularly extensive visual coverage of the measuring chamber region by the camera, shown here by way of example with the aid of the recording angle range 27b of the double camera unit 23b. It includes the field of view 25 for instance, in other words the region in which tomography recordings are implemented by the tomography arrangement 1. The second double camera unit 23a likewise records the measuring chamber 3 from the other side of the measuring chamber 3. It is therefore possible with the aid of a switching apparatus 14 to toggle between the operation of the two double camera units 23a, 23b and/or the display of the images recorded by the two double camera units 23a, 23b. The monitoring facility 9c also includes an automatic movement recognition unit 12, which is also used for the image output unit 13, so that movements of the patient 7 can be promptly identified.

Figure 4:
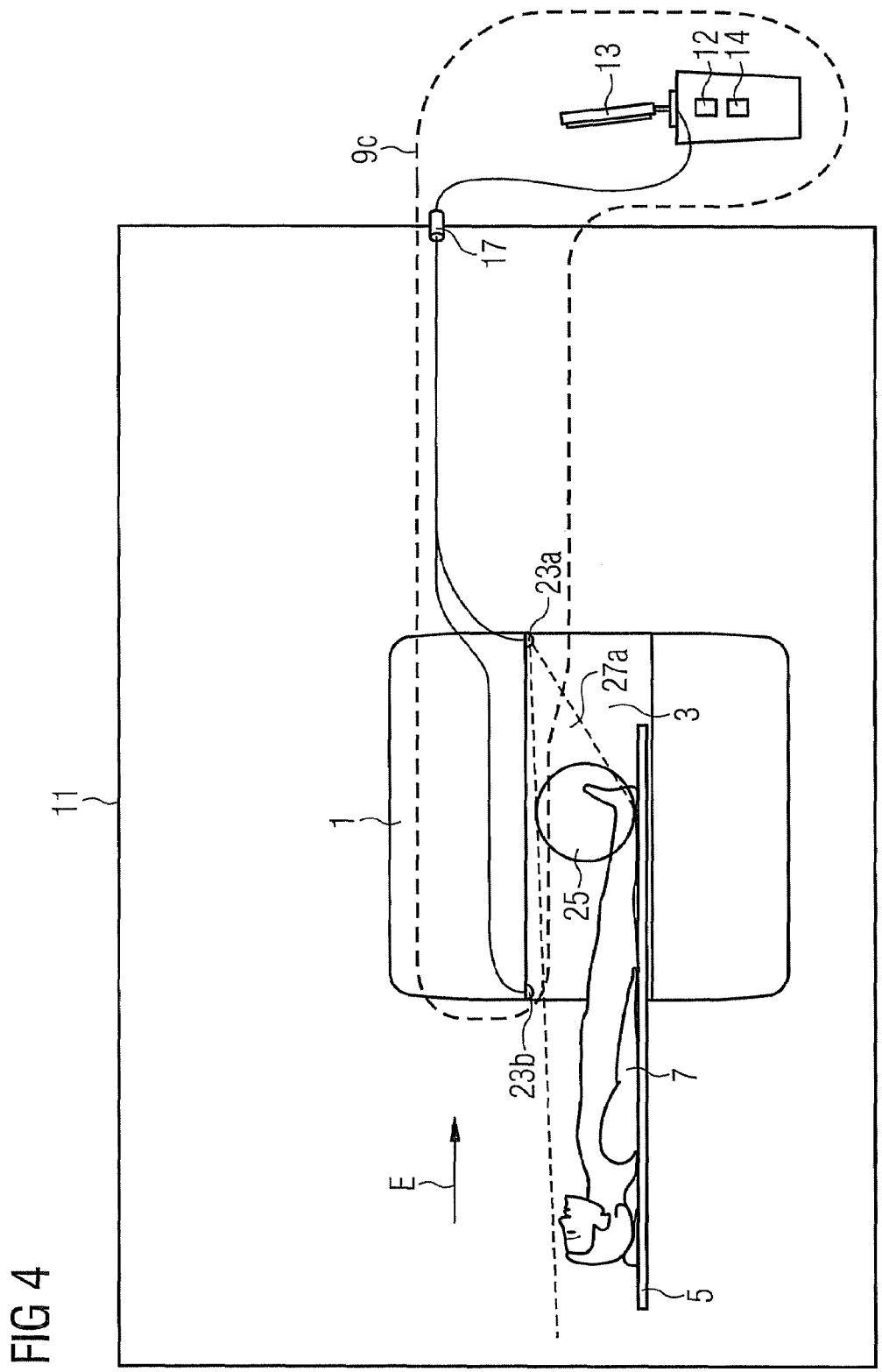
FIG. 4 shows a schematic display of the same embodiment of an inventive tomography arrangement as in FIG. 3 with another positioning of a patient.

FIG. 4 shows the same tomography arrangement 1 as in FIG. 3, with the patient 7 now being positioned in another position. He now moves feet first into the measuring chamber 3 in the insertion direction E. The recording angle range 27a of the double camera unit 23a can also be seen. Similarly to FIG. 3, it is apparent that the double camera units 23a, 23b positioned in the upper area of the measuring chamber 3 practically enable an optimal visual coverage of the overall measuring chamber 3 when combined. The patient 7 can be viewed in particular from both perspectives. If movements are not detectable for the camera of the one double camera unit, for instance because they are covered by the head of the patient, they can in any case be recorded by the cameras of the other double camera unit respectively. Furthermore, one of the cameras can record the facial region of the patient 7.

FIG. 5 shows, viewed from the interior of the measuring chamber, a double camera unit 23, which is attached to a tomography housing 29 of a magnetic resonance tomography arrangement 1 in the upper region of a measuring chamber 3. It essentially corresponds to the double camera units 23a, 23b shown in FIGS. 3 and 4. It also comprises from outside inwards:

two infrared LEDs 31, which are used as a first illumination facility,
two normal light LEDs 33, which are used as a second illumination facility,
in the centre a first video camera 35 to the left and a second video camera 37 to the right.

The first video camera 35 operates in the non-visible light wave range, while the second video camera 37 operates in the visible light wave range. A switchover facility 30 for switching between an operation of the first video camera 35 and the second video camera 37 is arranged within the double camera unit 23. This can also be localized within other elements in the monitoring facility 9c, for instance in a separate activation unit (not shown).

FIG. 6 shows a detailed schematic longitudinal section through the double camera unit 23 according to FIG. 5 with a part of the tomography housing 29 of the tomography arrangement 1 to better display the integration into the tomography housing 29. A gradient coil 39 and a basic field magnetic coil 41, shown here schematically, are located in the tomography housing 29 of the tomography arrangement 1. The double camera unit 23 is integrated into the tomography arrangement 1 such that it is mounted between the outer wall casing of the tomography housing 29 and the gradient coil 39 and/or basic field magnet coil 41. A minimal support depth of below 20 mm can be achieved as a result.

The double camera unit 23 is connected to current supply cables and optical wave guides to accept image data, which is shown here as a supply line combination 43 (a more precise explanation of the supply of the double camera unit 23 and the reading out of the recorded image data is to follow on the basis of FIG. 7) and has, inter alia, the following schematically drawn components: an EMC filter 45, a camera electronics system 49 on a printed circuit board, a flexible connector 51, a CCD chip 53, an infrared filter 55, a miniature wide angle lens 57 as well as a light-emitting diode 59 and an optical extension 61 for the light-emitting diode 59. The overall double camera unit 23 is surrounded by a high frequency shield 47, which shields the double camera unit 23 against electromagnetic interference radiation from the tomography arrangement 1 and vice versa. For interference suppression of the power supply of the camera electronics system 49, the EMC filter 45, in other words a filter, is used to ensure electromagnetic compatibility.

Other elements in the double camera unit 23 like for instance a second CCD chip, which is not positioned behind an infrared filter, cannot be identified due to the selected sectional plane. The section selected here only shows the essential elements which are needed to operate a first illumination facility and a first video camera 35, both of which operate in the non-visible light wave range.

The double camera unit 23 is configured such that it achieves as optimum a visual cover of a measuring chamber 3 as possible. It is therefore moveable in its lower range and connected to the camera electronics system 49 by way of the flexible connection 51. It can thus be pivoted within a certain angle in order to be able to adapt the recording range of the video camera.

The CCD-Chip 53 is used to record image information, while the infrared filter 55 only allows light through in the infrared range, so that in combination with the wide angle lens 57 and the camera electronics system 49 a first video camera 35, which operates, i.e. receives, in the non-visible light wave range, namely here in the infrared range, is produced.

The light-emitting diode 59 and its optical extension 61 (a type of thicker light guide) are used in a complementary fashion in respect of the first video camera 35 to illuminate the measuring chamber 3 with infrared light waves. At the same time, the light-emitting diode 59 can function as a sensor facility, which determines the existing brightness in the visible and/or in the non-visible range within the measuring chamber 3. An activation and/or deactivation circuit 60 is therefore linked to the light-emitting diode 56, the latter activating and/or deactivating the operation of the light-emitting diode 59 as an illumination facility. Similarly, the activation and/or deactivation circuit 60 can also switch other light-emitting diodes (not shown). It is similarly possible to switch between the IR video camera and the second video camera operating in the visible range as a function of the light situation thus recorded.

FIG. 7 shows a schematic block diagram of the monitoring facility 9. The following principal elements are shown here: a system control facility 63 in the form of a control processor, a user interface 65 and two double camera units 23a, 23b, with the double camera units 23a, 23b being located in an examination room 11 and the two first mentioned elements elsewhere, for instance in a monitoring room and/or a computer room.

The link between the user interface 65 and the two double camera units 23a, 23b takes place on the one hand by way of a power supply cable with a supply voltage $U_{Vers}$ and on the other hand by way of two optical fibers $VO_a$ and $VO_b$. The two optical fibers $VO_a$, $VO_b$ are routed into the examination room 11 by way of feedthrough waveguides $85_a$, $85_b$. The power supply cable is connected to the double camera units 23b, 23b by way of an EMC filter 45, with the EMC filter 45, which is attached here in the wall of the examination room, having the function of filtering interference influences by means of the tomography arrangement (not shown)—in the region here, as described in conjunction with FIG. 6.

The user interface 65 includes inter alia the following subunits used to operate the monitoring facility: a current supply interface 67, a logic unit 69, a level selection unit 71, a camera unit selection switch 73, a light spectrum selection switch 75, an image output unit 13 in the form of a monitor, which is connected to a signal processing unit 77, a video selection switch 79 as well as two signal converters 81a, 81b for conversion from optical signals into electrical signals.

The two double camera units 23a, 23b are identical in construction and each include the following subelements: a current supply input interface 87a, 87b, a signal converter 89a, 89b for converting electrical signals into optical signals, a level detector 91a, 91b, a signal conditioning unit 93a, 93b, a clock recovery generator unit 95a, 95b, an LED supply unit 97a, 97b, a switch 99a, 99b, two first light-emitting diodes 31a, 31b, two second light-emitting diodes 33a, 33b, a first CCD Chip 101a, 101b and a second CCD Chip 103a, 103b.

The system control facility 63 controls the overall process of monitoring persons in a measuring chamber 3 monitored by the double camera units 23a, 23b. It emits system proposals SV to the user interface 65 as an input in order to select the respective double camera units 23a, 23b.

The following processes in particular run in the user interface 65: a current supply of the user interface 65 and the double camera units 23a, 23b is provided by way of the current supply interface 67. The camera unit selection switch 73 is used to select the double camera unit 23a, 23b to be actuated in each instance. Three possible switch positions are provided here, for an automatic camera unit selection A, a first selection $M_{23a}$ of the first double camera unit 23a or a second selection $M_{23b}$ of the second double camera unit 23b. If an automatic camera unit selection A is switched, the logics unit 69 takes the system proposals SV of the system control facility 63 into account, on the other hand that double camera unit 23a or 23b, whose image data is to be indicated on the image output unit 13, is determined from the selection by way of the selection switch 73. The selection of the double camera unit 23a or 23b is forwarded via a switching signal MS to the video channel selection switch 79, which toggles between the inputs of the lines, which correspond to the optical fibers $VO_a$ and $VO_b$ and the signal converters 81a, 81b arranged downstream thereof. Image signals from only one of the two double camera units 23a, 23b correspondingly reach the signal conditioning unit 77 which actuates the image output unit 13. The image output unit therefore shows images which are derived from the respective image data of the selected double camera unit.

A selection is also made by way of the light spectrum selection switch 75 between a normal light operation NL and an infrared light operation IR. This switching information is further processed by the level selection unit 71 into different selection signals $S_{sel}$, which are encoded into different power supplies $U_{Vers}$. This means that two different direct current levels can be selected for the power supplies $U_{Vers}$, with the gauge level signaling whether an infrared light operation IR of the two double camera units 23a, 23b is selected or whether a normal light operation NL is selected. This encoding for distinguishing between an operation of the double camera units 23a, 23b with light in the visible light wave range (normal light operation NL) or with light in the non-visible light wave range (infrared light operation IR) is a particularly advantageous development of the invention provided additional control lines in the monitoring facility 9 can be spared and an effective and reliable selection of the respective operating mode is possible at the same time without a transmission of separate control signals being necessary which could disturb the magnetic resonance operation and/or would require additional filter expenditure The same procedure takes place in the two double camera units 23a, 23b as a function of signals received from the user interface 65:

The two double camera units 23a, 23b are supplied with operating current by way of the power supply input interfaces 87a, 87b. At the same time, the level detector 91a, 91b in the supply voltage $U_{Vers}$ decodes the information about the light wave range in which it is to be operated. It therefore conveys the selection signals $S_{sel}$, which are forwarded to the switch 99a, 99b, which as a function thereof either switches the first light-emitting diode 31a, 31b together with the first CCD-Chip 101a, 101b or switches the second light-emitting diodes 33a, 33b together with the second CCD chip CCD-Chip 103a, 103b. Here the LED supply unit 97a, 97b provides the respectively activated light-emitting diodes 31a, 31b and/or 33a, 33b with supply voltage. The image signals of the respectively activated CCD-Chips 101a, 101b or 103a, 103b reach the signal conditioning unit 93a, 93b, which in addition to the clock recovery generator unit 95a, 95b relate to a timing device for the clocked reading out of the image signals received by the CCD chips 101a, 101b or 103a, 103b.

The electrical image signals thus conditioned are converted by the signal converter 89a, 89b into optical signals and are transmitted to the user interface 65 by way of the optical $VO_a$ and $VO_b$.

The circuit structure shown here has a few special advantages: two structurally identical double camera units 23a, 23b are sufficient and can be easily mutually actuated accordingly. Secondly, this actuation essentially takes place by way of encoding the power supply $U_{Vers}$, the benefits of which were already mentioned. Thirdly, the monitoring facility can be controlled by way of a terminal, here therefore the user interface here 65, with its nevertheless being possible but not essential to take account of additional information relating to the system control facility 63. Fourthly, an automatically combined operation of a first video camera 35 takes place, the essential element of which is a first CCD chip 101a, 101b, with a first illumination facility 31, the essential elements of which are the light-emitting diodes 31a, 31b and similarly thereto a second video camera 37 with a second illumination facility 33 in each instance. The operation of the camera and corresponding illumination in the same light wave range is therefore coupled.

Reference is finally made again to the tomography arrangement described in detail above as well as to the corresponding method only being exemplary embodiments which can be modified by a person skilled in the art in the most varied of manners, without departing from the field of the invention. The use of the indefinite article "a" and/or "a" does not exclude the relevant features from also being present in multiples.

The invention claimed is:

1. A tomography arrangement, comprising:
   a measuring chamber;
   a housing; and
   a monitoring device that monitors an object in the measuring chamber, the monitoring device comprising a double camera unit with at least two of the following components in a common housing:
      a first illumination unit that illuminates the measuring chamber in a non-visible light wave range;
      a first video camera that operates in the non-visible light wave range and records a first image of the object;

a second illumination unit that illuminates the measuring chamber in a visible light wave range; and a second video camera that operates in the visible light wave range and records a second image of the object, wherein the double camera unit is mounted between an outer wall casing of the housing and a gradient coil of the tomography arrangement, and wherein the double camera unit is surrounded by a high frequency shield for shielding electromagnetic interference radiation from the tomography arrangement.

2. The tomography arrangement as claimed in claim 1, wherein the non-visible light wave range comprises an infrared range.

3. The tomography arrangement as claimed in claim 1, wherein the monitoring device comprises a switchover unit between the first video camera and the second video camera.

4. The tomography arrangement as claimed in claim 3,
wherein the monitoring device comprises a sensor unit coupled to the switchover unit that determines brightness in the measuring chamber, and wherein the switchover unit automatically switches over an operation between the first video camera and the second video camera as a function of the brightness.

5. The tomography arrangement as claimed in claim 1, wherein the first video camera or the second video camera is directly attached to the housing of the tomography arrangement in an input region of the measuring chamber or an output region of the measuring chamber.

6. The tomography arrangement as claimed in claim 1, wherein the first video camera or the second video camera is attached to an upper region of the measuring chamber.

7. The tomography arrangement as claimed in claim 1, wherein the first video camera or the second video camera is attached at an end of the measuring chamber.

8. The tomography arrangement as claimed in claim 1,
wherein the first video camera is coupled to the first illumination unit so that the first video camera and the first illumination unit are operated automatically together, and wherein the second video camera is coupled to the second illumination unit so that the second video camera and the second illumination unit are operated automatically together.

9. The tomography arrangement as claimed in claim 1, wherein the monitoring device comprises an automatic movement detection unit that detects a movement of the object based on the first image or the second image.

10. The tomography arrangement as claimed in claim 1, wherein at least one of the first video camera and the second video camera comprises a wide angle lens.

11. The tomography arrangement as claimed in claim 1, wherein at least one of the first video camera and the second video camera is a multispectral camera and comprises a light wave filter.

12. The tomography arrangement as claimed in claim 1, wherein the monitoring device comprises a first double camera unit and a second double camera unit that are attached at two ends of the measuring chamber respectively.

13. The tomography arrangement as claimed in claim 12, wherein the monitoring device comprises a camera unit selection switch that selects one of the first double camera unit and the second double camera unit to be actuated.

14. A method for monitoring an object in a measuring chamber of a tomography arrangement, comprising:
illuminating the measuring chamber in a non-visible light wave range by a first illumination unit;

operating a first video camera in the non-visible light wave range;

recording a first image of the object by the first video camera;

illuminating the measuring chamber in a visible light wave range by a second illumination unit;

operating a second video camera in the visible light wave range;

recording a second image of the object by the second video camera;

mounting a double camera unit between an outer wall casing of a housing of the tomography arrangement and a gradient coil of the tomography arrangement; and surrounding the double camera unit by a high frequency shield for shielding electromagnetic interference radiation from the tomography arrangement;

displaying the first and/or the second image; and monitoring the object based on the first and/or the second image, wherein the double camera unit comprises at least two of the following components in a common housing: the first illumination unit, the first video camera, the second illumination unit, and the second video camera.

15. The method as claimed in claim 14, further comprising switching over an operation between the first video camera and the second video camera.

16. The method as claimed in claim 15, wherein the measuring chamber is illuminated as a function of the respective light wave range in which the first video camera or the second video camera is operated.

* * * * *